United States Patent [19]
Denzler

[11] Patent Number: 5,677,140
[45] Date of Patent: Oct. 14, 1997

[54] PROCESS AND TEST KIT FOR DETERMINING THE BACTERIAL COUNT LEVEL IN WHEY AND WHEY PRODUCTS

[75] Inventor: Hans-Joerg Denzler, Langelsheim, Germany

[73] Assignee: Biolac GmbH, Harbarnsen, Germany

[21] Appl. No.: 594,316

[22] Filed: Jan. 30, 1996

Related U.S. Application Data

[63] Continuation-in-part of Ser. No. 43,217, Apr. 6, 1993, abandoned.

[30] Foreign Application Priority Data

Apr. 13, 1992 [EP] European Pat. Off. .............. 92106340

[51] Int. Cl.$^6$ .............. C21Q 1/04; C21Q 1/66; C21Q 1/00; G01N 21/76
[52] U.S. Cl. .............. 435/34; 435/8; 435/6; 435/968; 435/4; 436/172; 536/1.11; 536/123.13; 536/124
[58] Field of Search .............. 435/34, 8, 6, 968, 435/4; 436/172; 536/1.11, 123.13, 124

[56] References Cited

U.S. PATENT DOCUMENTS 3,616,253  10/1971  Eustachio ..................... 435/8

FOREIGN PATENT DOCUMENTS

| 0299601 | 1/1989 | European Pat. Off. . |
| 0309429 | 3/1989 | European Pat. Off. . |
| 0441469 | 8/1991 | European Pat. Off. . |
| 9200317 | 1/1992 | European Pat. Off. . |
| 2001434 | 1/1979 | United Kingdom . |

OTHER PUBLICATIONS

Maikamaki et al; "J. Vet. Med. B", vol. 33, pp. 174–179, 1986. Month of Publication Not Available.

Busch et al, "Dechema Biotech Conferences 4", pp. 953–957, 1990. Month of Publication Not Available.

*Primary Examiner*—Louise Leary
*Attorney, Agent, or Firm*—Evenson, McKeown, Edwards & Lenahan P.L.L.C.

[57] ABSTRACT

A process for rapidly determining the bacterial count level in whey or whey constituents by adding a bacteria lysing reagent and then a luciferin-luciferase reagent to a sample to be analyzed at a pH from 7.0 to 7.9 and then measuring the bioluminescence light emitted from the luciferase-luciferin reaction, and an analysis kit for carrying out the process.

11 Claims, No Drawings

PROCESS AND TEST KIT FOR DETERMINING THE BACTERIAL COUNT LEVEL IN WHEY AND WHEY PRODUCTS

CROSS REFERENCE TO RELATED APPLICATION

This application is a continuation-in-part of application Ser. No. 08/043,217, filed Apr. 6, 1993 now abandoned.

BACKGROUND OF THE INVENTION

This invention relates to a process for rapid determination of the bacterial count level in whey and whey constituents using the luciferin-luciferase bioluminescence reaction, and also to an analysis kit for performing this process in whey.

The processing of whey and whey constituents requires constant monitoring of the microbiological quality of the raw materials used, in order that microbial contamination of the end products produced therefrom can be ruled out. In dairies and milk-processing factories, therefore, microbiological tests are performed continuously before, during and after processing, by means of which tests the starting products which are processed and the end products which are produced, for example whey and whey products obtained from whey such as lactose or whey protein powder, can be investigated for the presence of undesirable bacteria. In these tests it is often necessary to be able to detect very low bacteria densities of numerous different types of microorganisms.

One method which has been used in the past to determine the bacterial count in dairy products is the so-called Koch plate process. In this method, the samples to be investigated are smeared onto agar plates and incubated at 30° C. for about 72 hours. A conclusion about the bacterial count in the samples being investigated can then be drawn from the number of colonies which have grown on the agar plates. This determination method is not only very time-consuming, but also very costly, since until the agar plates are evaluated, the corresponding supply of raw material has to be temporarily stored under refrigerated conditions for this period.

Kolehmaine, Published German Patent Application No. DE 2,831,559 (Feb. 15, 1979) discloses a process for determining somatic cells in milk. This process is based on the known luciferin-luciferase reaction in which adenosine triphosphate (hereinafter abbreviated ATP) is reacted enzymatically to adenosine monophosphate (hereinafter abbreviated AMP). The bioluminescence which occurs during this reaction is measured quantitatively, with the quantity of light which is being released being proportional to the quantity of ATP contained in the sample. Since each cell contains ATP, the number of somatic cells can be calculated from the ATP concentration by correlating the measured value from the test sample against a known standard.

The ATP content is characteristic for each type of cell. Thus bacteria cells contain far less ATP than the substantially larger somatic cells.

SUMMARY OF THE INVENTION

It was an object of the invention to provide a process for rapid determination of the bacterial count level in whey and whey constituents with which the bacterial density can be rapidly determined.

It was also an object of the invention to provide a process which would reduce the large number of test containers, such as petri dishes, which had to be used to determine the bacterial count of whey or a whey constituent.

These and other objects of the invention are achieved by providing a process for rapid determination of the bacterial count level in a sample of whey or whey constituents to be analyzed, the process comprising:

a) preparing the sample for bioluminescence measurement by
  aa) wherein the sample is whey,
    aa1) diluting the whey sample with a reagent solution containing ethoxylate of 4-(1,1,3,3-tetramethylbutyl)phenol;
    aa2) separating the diluted whey sample by centrifugation into a liquid phase and an solid residue;
    aa3) converting the solid residue into a suspension by adding a reagent solution containing a bacteriolytic reagent;
    aa4) forming a reaction mixture by mixing the suspension with a reagent solution which hydrolyzes adenosine triphosphate;
    aa5) allowing the reaction mixture from step aa4) to react for a time sufficient to hydrolyze adenosine triphosphate present therein and to inactivate excess adenosine triphosphate hydrolyzing reagent;

or ab) wherein the sample is a whey constituent,
    ab1) introducing the whey constituent sample into an aqueous, isotonic salt solution;
    ab2) filtering the solution containing the sample through a sterile filter;
    ab3) transferring the filter with retained bacteria thereon into a nutrient solution suitable for culturing bacteria; incubating this solution for 1 to 9 hours at 28° C. to 38° C., and subsequently using the nutrient solution from above the filter as a reaction mixture for further measurement;

b) releasing bacterial adenosine triphosphate in the reaction mixture obtained from process steps aa1) to aa5) or ab1) to ab3) by treatment with a reagent which releases bacterial adenosine triphosphate;

c) adding to the reaction mixture a luciferin-luciferase reagent solution buffered to a pH value of from 7.0 to 7.9 in order to effect a bioluminescence reaction with released adenosine triphosphate;

d) photometrically quantitatively measuring light emitted during the bioluminescence reaction, and e) determining the bacterial count level in the sample to be analyzed by comparing the measured light quantity with a standard curve produced under the same conditions with a sample of similar origin having a known bacterial count level.

In accordance with a further aspect of the invention, the objects are also achieved by providing an analysis kit for determining the bacterial count level in whey in which a whey sample is diluted with a reagent solution containing ethoxylate of 4-(1,1,3,3-tetramethylbutyl)phenol, the diluted sample is separated by centrifugation into a liquid phase and a solid residue, the solid residue is converted to a suspension by introducing it into a reagent solution containing a bacteriolytic reagent, the suspension is mixed with an adenosine triphosphate hydrolyzing reagent solution to form a reaction mixture, the reaction mixture is allowed to react for a time sufficient to react and to inactivate excess adenosine triphosphate hydrolyzing reagent, bacterial adenosine triphosphate in the reaction mixture is released by treatment with a reagent which releases bacterial adenosine triphosphate, a luciferin-luciferase reagent solution buffered to a pH of 7.0 to 7.9 is added to the reaction mixture in order to effect a bioluminescence reaction with released adenosine triphosphate, light emitted during the bioluminescence reaction is photometrically measured, and the bacterial count level in the whey sample to be analyzed is determined by comparison with a standard curve produced under the same conditions from a whey sample of similar origin having a known bacterial count; the analysis kit comprising:

a) a reagent solution containing ethoxylate of 4-(1,1,3,3-tetramethylbutyl)phenol;

b) a bacteriolytically active reagent solution;

c) reagents for preparing an adenosine triphosphate hydrolyzing reagent solution, namely:
  c1) somase in freeze-dried form;
  c2) ethylenediaminetetraacetic acid disodium salt in solid form, and
  c3) a liquid solution of a reagent for releasing nucleotides from somatic cells;

d) a bacterial adenosine triphosphate releasing reagent solution;

e) a luciferin-luciferase reagent, and f) a buffer solution buffering at a pH of 7.0 to 7.9.

DETAILED DESCRIPTION OF PREFERRED EMBODIMENTS

In accordance with the present invention, a process has been devised by means of which bacterial contamination in whey and whey constituents can be detected with the aid of the luciferin-luciferase bioluminescence method. Whey is a byproduct in the production of cheese or casein, and the microorganism population found in whey is distinctly different from the microorganism population found in raw milk.

As a rule in the production of cheese, first the original microorganisms of the milk are essentially all killed by heat treatment. By addition of, for example, nitrate ions, other microorganisms (e.g. Clostridia) can be eliminated. Subsequently, the casein of the milk is caused to curdle or coagulate. This can be achieved by lactic acid fermentation in which individually added starter bacteria cultures partially break down the milk sugar (lactose) to lactic acid, or by addition of rennin or chymase enzyme, or by a combination of both procedures. During the coagulation, casein micelles are generated which form a three-dimensional network and enclose the remaining constituents of the milk. This network is referred to as "coagulum". As soon as the coagulum has attained the desired consistency, it is cut into pieces. By means of further processing steps the coagulum is caused to release a large portion of the enclosed aqueous liquid with the various materials dissolved therein (primarily lactose, whey protein and salts), namely the whey.

As used herein, the term "whey" is to be understood to include, in addition to the sweet whey formed during the production of cheese, also whey concentrate and diluted whey. As used herein, the term "whey constituents" is understood to include all constituents obtainable from whey, in particular lactose and whey protein, for instance lactose powder or whey protein powder such as whey protein concentrate powder.

The invention thus relates to a process for rapid determination of the bacterial count level of a sample of a whey or whey constituent, in which the sample preparation method depends on the nature of the sample to be analyzed. The process is characterized in that:

a) The sample is prepared for bioluminescence measurement by aa) wherein the sample is whey,
  aa1) the whey sample is diluted with a reagent solution containing the ethoxylate of 4-(1,1,3,3-tetramethylbutyl)phenol,
  aa2) the diluted whey sample is separated by centrifugation into a liquid phase and a solid residue,
  aa3) the solid residue is converted into a suspension by addition of a reagent solution which contains a bacteriolytic reagent,
  aa4) the suspension is mixed with an ATP-hydrolyzing reagent solution to form a reaction mixture,
  aa5) the resulting reaction mixture is allowed to react for a time sufficient to react and to inactivate excess ATP-hydrolyzing reagent solution in the range of about 20 minutes, ab) or wherein the sample is a whey constituent,
  ab1) the whey constituent sample is introduced into an aqueous isotonic salt solution,
  ab2) the solution containing the sample is filtered through a sterile filter,
  ab3) the filter with bacteria retained thereon is transferred to a nutrient solution suitable for cultivation of bacteria, and is incubated in this nutrient solution for 1 to 9 hours at 28° C. to 38° C., and subsequently the nutrient solution above the filter is used as the reaction mixture for further measurement, b) in the reaction mixture obtained after carrying out process steps aa1) through aa5) or ab1) through ab3), bacterial ATP is released by treatment with a reagent solution which releases bacterial ATP, c) a luciferin-luciferase reagent solution buffered to a pH value of 7.0 to 7.9 is added to the reaction mixture in order to effect a bioluminescence reaction with released ATP, d) the amount of light emitted during the bioluminescence reaction is determined photometrically, and e) the bacterial count level in the sample to be analyzed is determined by comparison with standard curves produced under the same conditions from samples of similar origin having known bacterial counts.

In carrying out the process with a sample of whey to be analyzed, the whey sample is initially diluted in process step aa1) with a reagent containing the ethoxylate of 4-(1,1,3,3-tetramethylbutyl)phenol in order to prepare the sample. The content of ethoxylate of 4-(1,1,3,3-tetramethylbutyl)phenol in the reagent solution is sufficient to provide in the sample a concentration which is capable of opening the cell membranes of somatic cells and releasing somatic ATP. Usually, a commercially available, known Triton X-100 reagent is used. In a preferred embodiment, this reagent solution additionally contains chemical detergents and emulsifiers.

In process step aa2) the diluted solution of the whey sample is centrifuged in order to separate it into a liquid phase and a solid residue. The centrifugation may advantageously be carried out for a duration of from 3 to 7 minutes, preferably 5 minutes, with a centrifugal force of 8,000×g to 16,000×g, preferably 12,000×g.

In process step aa3) the separated solid residue is converted into a suspension by addition of a bacteriolytic reagent solution. A suitable bacteriolytic reagent solution is, for example, an aqueous solution of a bacteriolytically active enzyme, for example lysozyme, and a chemical stabilizer.

In order to hydrolyze ATP, physical, chemical or enzymatic methods are suitable. Preferably, in process step aa4)

the suspension is treated with a combination of an enzyme, preferably an ATPase such as somase, and a reagent capable of releasing nucleotides from somatic cells. The nucleotide releasing reagent may suitably be the known "Nucleotide Releasing Reagent for Somatic Cells" (hereinafter abbreviated as "NRS-Reagent"), which consists essentially of an aqueous solution of 2 to 7 wt. % trichloroacetic acid to which a complexing agent for divalent cations, such as the disodium salt of ethylenediaminetetraacetic acid (hereinafter abbreviated $Na_2EDTA$), is added in a concentration of 3 to 4 mg per 1 ml of solution. Preferably, the NRS Reagent solution contains 5 wt. % trichloracetic acid and $Na_2EDTA$ which is added in a concentration of about 42 mg per 11.2 ml of solution.

In process step aa5) the added ATP-hydrolyzing reagent solution is inactivated by allowing the sample to stand for a sufficient time in the range of approximately 20 minutes, so that subsequently released bacterial ATP is not broken down enzymatically. In order to complete the reaction, the sample is advantageously shaken during this time on a suitable automatic shaking apparatus at approximately 600 to 800 cycles per minute.

If the process is carried out with a sample of a whey constituent which is to be analyzed, the sample for the bioluminescence measurement is prepared in a manner which differs from the procedure for a whey sample which is to be analyzed. In carrying out process steps ab1) through ab3) the following steps are carried out sequentially: the sample to be analyzed is sterile filtered, the filter is transferred to a nutrient solution suitable for cultivation of bacteria and after incubation of 1 to 9 hours, in particular 1 to 3 hours, at temperatures suitable for cultivation of bacteria, such as between 28° C. and 38° C., for example at 35° C., the remainder of the process in accordance with process steps b) through e) is subsequently carried out with the nutrient solution from above the filter. By means of these process steps, the bacterial population is amplified in an advantageous manner so that the process of the invention is capable of detecting even very low levels of bacterial contamination in whey and whey constituents.

The release of the bacterial ATP in process step b) is achieved for a reaction mixture prepared according to process steps aa1) to aa5) or ab1) to ab3) by treating the reaction mixture with a reagent suitable for lysis of bacteria cell membranes. The lysis may be effected enzymatically, e.g. by treatment with lysozyme, for example with a solution of lysozyme and approximately 1.5% by weight trichloroacetic acid, or chemically, for example by detergents suitable for solubilizing bacteria membranes. Preferably a known, so-called "Nucleotide Releasing Reagent for Microbial Cells" (hereinafter abbreviated as NRB reagent) is used. An NRB reagent may be a solution which contains an ionic detergent in a concentration of approximately 0.1 to 2% by weight.

In process step c), a luciferin-luciferase reagent solution buffered to a pH of 7.0 to 7.9 is used. The luciferin-luciferase reagent is known and can be obtained from organisms capable of bioluminescence. In particular, luciferin-luciferase reagent obtained from glowworms may be used. Such luminescence reagents are generally commercially available. As buffers, various buffer systems which buffer in a physiological pH range from 7.0 to 7.9 may be used, for example, phosphate buffer or N-2-hydroxyethylpiperazin-N'-2-ethanesulfonic acid buffer (hereinafter abbreviated as HEPES buffer). Preferably the known "Lumit"™ buffer from the firm Lumac Systems of Basel, Switzerland, is used which contains 25 mmole/liter HEPES buffer, 7.5 mmole/liter magnesium sulfate and 1 mmole/liter $Na_2EDTA$.

Commercially-available photon-measuring apparatus, e.g. photometers or photon-counters, may be used in order to measure the quantity of bioluminescence light in process step d). Since it is necessary to be able to detect very small quantities of light, it is especially advantageous to use a photon-counter, particularly a photon-counter suitable for measuring individual photons. After process step d), a process step e) is carried out. In this step the bacterial count level of the sample to be analyzed as determined according to the process of the invention is compared with standard curves which have been produced from samples of similar origin having known bacterial counts. The bacterial counts of these reference samples are determined according to the Koch plate procedure.

The comparison of the measured values determined according to the process of the invention with the standard curves makes possible a rapid and reliable determination of the bacterial count level.

The measured amount of bioluminescence light from the samples being analyzed can also be related to a standard ATP concentration for which the amount of bioluminescence light has previously been quantitatively determined under identical measuring conditions. Before the actual measurements are made, a so-called method blank value is determined for the solutions and reagents used without samples to be analyzed, using the same photon measuring apparatus. The resulting measured values must be corrected by the method blank value in order to calculate the actual quantity of bioluminescence light of the samples to be analyzed.

The method according to the invention for determining the bacterial count level in a whey constituent, particularly in lactose powder, can advantageously be performed by dissolving the sample to be analyzed in an approximately 8-fold to 12-fold quantity of sterile isotonic solution, e.g. Ringer's solution, and heating the solution to 40° to 60° C. in a water bath with slight shaking for approximately 20 to 40 minutes. The solution is then filtered through a sterile vacuum filter and subsequently rinsed with an approximately 5-fold to 10-fold quantity of sterile isotonic solution. Then the filter is transferred to a sterile vessel, e.g. a Petri dish; covered with a sterile bacterial nutrient solution, and incubated for approximately 30 to 120 minutes at 28° C. to 38° C., preferably at 35° C. The nutrient solution standing above the filter is then used as the reaction mixture for further measurements. In order to release the bacterial ATP from the bacteria cells, approximately 0.5 to 2 parts by volume of a so-called NRB reagent solution as defined above is added for each part by volume of nutrient solution used to cover the filter. For example, a 0.1 to 2% aqueous solution of an ionic detergent or an aqueous solution which contains approximately 1 to 2% by weight trichloroacetic acid and also the enzyme lysozyme may be used as an NRB reagent solution. After addition of the NRB reagent, the solutions are thoroughly mixed, for example by carefully swirling the Petri dish, and after 1 to 2 minutes an aliquot of 50 to 500 µl, preferably 200 µl, is removed and pipetted into a transparent cuvette. The cuvette used should have high permeability to the bioluminescence light (562 nm) which is to be detected. The cuvette is inserted into a photon measuring apparatus suitable for measuring luminescence. Then 10 to 1000 µl, preferably 100 µl, of known luciferin-luciferase reagent are added to the solution in the cuvette, and the resulting bioluminescence released in the sample is measured quantitatively. The number of bacteria in the sample is then calculated from the measured quantity of bioluminescence light using a correlation factor determined from the measured bioluminescence of a known standard.

The process according to the invention can also be carried out to determine the bacterial count in whey protein powder in the same manner as described for lactose powder.

The process according to the invention is advantageously carried out in a sample of whey to be analyzed in such a way that one volume portion of the whey sample is transferred to a container suitable for carrying out the rest of the process, preferably a centrifuge tube, and diluted with approximately one/half volume portion of a reagent solution containing the ethoxylate of 4-(1,1,3,3-tetramethylbutyl)phenol. After the diluted whey sample is intimately mixed, for example by repeated shaking of the container, the container is placed in a centrifuge. The sample is centrifuged for approximately 3 to 10 minutes at about 8,000×g to 16,000×g and room temperature. Thereafter, the mostly clear supernatant (liquid phase) is separated from the solid residue. This can be achieved, for example, by carefully withdrawing the liquid phase with a pipette. The remaining solid residue is added to approximately one/fifth volume portion of a bacteriolytic reaction solution, and the resulting mixture is repeatedly resuspended. Approximately one/twenty-fifth volume portion of an ATP-hydrolyzing reagent solution is further added to the resuspended mixture. Then the sample prepared in this manner is shaken on a suitable mechanical shaker at approximately 400 to 1,000 cycles per minute for a time sufficient for reaction and inactivation of the ATP-hydrolyzing reagent solution in the range of approximately 20 minutes. An aliquot of 10 to 1,000 µl, preferably 100 µl, is withdrawn from the shaken sample and pipetted into a transparent cuvette. The subsequent procedure is carried out in a manner identical to the procedure followed in case of a sample of lactose powder to be analyzed.

The process according to the invention advantageously enables the luciferin-luciferase bioluminescence method to be used for rapid determination of the bacterial count level in whey and whey constituents. Examples of whey products in which the bacterial count can be determined rapidly and reliably using the process according to the present invention include, in particular, lactose powder and whey protein powder. The process according to the invention can be performed considerably more rapidly than the conventional Koch plate process.

The invention further comprises an analysis kit for carrying out the described process for determining the bacterial count in whey. The analysis kit contains:

a) a reagent solution which contains the ethoxylate of 4-(1,1,3,3-tetramethylbutyl)phenol, b) a reagent solution having a bacteriolytic effect, c) reagents for preparing an ATP-hydrolyzing reagent solution, namely:

c1) somase in freeze-dried form, c2) $Na_2EDTA$ in solid form, c3) an NRS-reagent solution from which an ATP-hydrolyzing solution can be produced by addition of the $Na_2EDTA$ and subsequent addition of the resulting reagent solution to the somase dissolved in buffer solution, d) a reagent solution which releases bacterial ATP, e) a luciferin-luciferase enzyme reagent in freeze-dried form, f) a buffer solution which buffers at a pH value of 7.0 to 7.9 for dissolving reagents c1) and e).

By using an analysis kit according to the invention, which represents a combination of the aforementioned reagents, it is possible make use of the luciferase-luciferin reaction to quickly and reproducibly determine the bacterial count level in whey.

It is surprising that it is possible at all to determine the bacterial count level in whey or whey constituents using the process of the invention, since bacteria cells contain far less ATP than, for example, somatic cells or yeast cells. It is also surprising that it is possible in the process according to the invention to detect the luciferin-luciferase bioluminescence even at a low bacterial density. It is very surprising that so-called chemical quenching, caused, for example, by the whey constituents, and optical quenching, caused by the high coloration or cloudiness of the samples derived from whey, do not occur to any significant extent. The process according to the invention and the analysis kit according to the invention for performing this process thus provide a method with which a reliable evaluation of the bacterial germ content of whey and whey constituents can be made quickly and reproducibly and at low cost in terms of time and space.

The following examples are intended to illustrate the invention in further detail without limiting its scope.

EXAMPLES

In the following examples, a Biocounter M2500, manufactured by Lumac Systems of Basel, Switzerland was used as a photon-counter for quantitatively determining the bioluminescence. The Biocounter M2500 has a bialkaliphotocathode with which light having a wavelength from 350 to 650 nm can be measured at a maximum counting rate of 50,000 units per second. The apparatus was calibrated using a 200 picogram ATP-Standard under the conditions described below for analysis of the samples. Before each sequence of measurements, the injection systems and the cuvettes were rinsed at least four times with sterile distilled water. All measurements made on the apparatus were performed under conditions which were as sterile as possible.

All the reagents, nutrient solutions and buffer solutions used were prepared with sterile media. Nutrient solutions were autoclaved before use. The bioluminescence blank values for all the reagents, buffers and nutrient solutions used were determined in preliminary tests.

Reagents, buffers and nutrient solutions used:

1. Ringer's solution:

A known isotonic solution of sodium chloride, referred to as Ringer's solution, is composed of an aqueous solution of 0.8% by weight NaCl, 0.02% by weight KCl, 0.02% by weight $CaCl_2$ and 0.1% by weight $NaHCO_3$.

2. Buffer solution buffering at a pH value of 7.0 to 7.9:

As buffer solution in the experiments described here, a buffer commercially available from the firm Lumac Systems AG under the name "Lumit"™ having a pH value of 7.75, was used. This buffer is composed of 25 mmole/liter HEPES buffer, 7.5 mmole/liter magnesium sulfate and 1 mmole/liter EDTA.

3. Reagent solution containing an ethoxylate of 4-(1,1,3,3-tetramethylbutyl)phenol:

A reagent solution commercially available from the firm Promega was utilized which in addition to the active ingredient known as Triton X-100, also contained additional chemical emulsifiers and detergents.

4. Reaction solution containing a bacteriolytic reagent:

A solution commercially obtained from the firm Promega, containing lysozyme (muramida mucopeptide glucohydrolase) and chemical stabilizers, was used.

5. ATP hydrolyzing solution:

The reagent which was used was prepared from commercially available, freeze-dried somase from Lumac Systems AG of Basel, Switzerland, solid $Na_2EDTA$ and a commercially available NRS solution. The somase was reconstituted before use with a suitable buffer. A commercially available buffer sold under the name "Lumit"™, manufactured by Lumac Systems AG was used for this purpose. 2 ml of buffer solution were added to a packet containing 6.4 units of freeze-dried somase to prepare the somase solution. In addition an NRS-reagent solution and solid $Na_2EDTA$ were added. An aqueous solution of 5% by weight trichloroacetic acid and 42 mg/11.2 ml EDTA can be used. In the following tests, the commercially available reagent solution "NRS"™, manufactured by Lumac Systems AG was used.

6. Solution of bacterial ATP releasing reagent (NRB-reagent):

An aqueous solution of an ionic detergent having a concentration of 0.1 to 2% by weight can be used as the NRB reagent. In the following tests, the commercially available reagent "L-NRB"™, manufactured by Lumac Systems of Basel, Switzerland, was used.

7. Luciferin-luciferase reagent solution:

Glowworm luciferin-luciferase reagent is commercially available in freeze-dried form. The commercially available products usually additionally contain bovine serum albumin and dithiothreitol. The luciferin-luciferase reagent sold under the name "Lumit-PM"™ by Lumac Systems AG of Basel, Switzerland, was used for the measurements described in the examples. The ready-to-use solution of luciferin-luciferase reagent was produced by dissolving the freeze-dried luciferin-luciferase reagent in a Lumit™ buffer having a pH value of 7.75.

8. Bacterial nutrient solution:

In order to activate the bacterial cell activity and to amplify samples which were only slightly contaminated, the commercially available nutrient solution called "Lumacult"™, manufactured by Lumac Systems AG of Basel, Switzerland, was used as the bacterial nutrient solution in the following examples.

I. Measurement of the bacterial count in lactose powder.

11 g of lactose powder were weighed under sterile conditions into 99 ml of Ringer's solution diluted with sterile distilled water (0.25-fold concentrated). The sample solution was shaken several times and heated for 30 minutes in a water bath at a temperature of approximately 50° C. During this period, the sample was stirred several times. Then the solution was filtered in the warm state through a sterile vacuum filter (pore diameter 0.45 µm, Pall-positive-filter) and was subsequently rinsed with approximately 50 ml of Ringer's solution. The filter was placed in a sterile Petri dish and was completely covered with 0.5 ml of bacterial nutrient solution. After the Petri dish had been incubated for 80 minutes at approximately 35° C., 0.5 ml of NRB reagent was added. Then the dish was carefully swirled for another 90 seconds. For better mixing, 200 µl of the filter residue were drawn up and let out again 3 times with a sterile pipette. Then 200 µl of the sample were poured into a cuvette and inserted into the photon-counter. 100 µl luciferin-luciferase reagent were added automatically via the injection system of the photon-counter, and the quantity of bioluminescence light was measured. The measured quantity of light was displayed as an RLU value (RLU=relative light units) by the photon-counter after 10 seconds' integration time. The quantity of ATP present in the sample could be calculated from the measured RLU values in relation to the RLU value of the ATP standard.

The bioluminescence blank value was determined by repeating the entire measurement under identical conditions without lactose powder.

II. Determination of the bacterial count in whey.

1 ml whey was pipetted into a suitable centrifuge tube, and 0.5 ml of the reagent containing Triton X-100 (Reagent 3 of the reagents, buffers and nutrient solutions used) was added with a micropipette. After intimate mixing of the diluted whey sample, the tube was centrifuged in a microcentrifuge at 12,000×g and room temperature for 5 minutes. The clear supernatant was removed in a pipette and discarded. To the solid residue (pellet) were successively added 0.2 ml of the reaction solution containing a bacteriolytic reagent (Reagent 4), and 40 µl of the ATP-hydrolyzing reagent solution (Reagent 5). The mixture subsequently was shaken on a shaker (Model IKA-Vibrax-VXR) at 600 to 800 cycles/min for approximately 20 minutes at room temperature. 100 µl of this solution were transferred into a further cuvette using a sterile pipette, and then the cuvette was inserted into the photon-counter. 100 µl of NRB reagent (Reagent 6) and then 100 µl of luciferin-luciferase reagent (Reagent 7) were added automatically via the injection system of the photon-counter, and the quantity of bioluminescence light was measured. After 60 seconds' integration time, an RLU value was displayed, from which the quantity of ATP present in the sample was calculated in relation to the RLU value of the ATP standard.

The bioluminescence blank value was determined as described in Example I.

III. Determination of bacterial count in whey protein powder 11 g of whey protein powder were weighed into 99 ml of Ringer's solution. This solution was allowed to stand for 20 minutes at 20° C. and shaken several times. 0.5 ml of the solution were withdrawn using a sterile pipette and transferred into a cuvette. After addition of 100 µl of a solution containing somase in the NRS reagent, and 0.4 ml Lumit™ buffer, the mixture was incubated for 40 minutes at room temperature. Then 100 µl were transferred using a sterile pipette into another cuvette, and this cuvette was inserted into the photon-counter. After the addition of 100 µl of NRB reagent and subsequent addition of 100 µl of luciferin-luciferase reagent via the automatic injection system of the photon-counter, the amount of bioluminescence light released was measured. After 60 seconds' integration time an RLU value was displayed from which the quantity of ATP present in the sample could be calculated in relation to the RLU value of the ATP standard.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A process for rapid determination of the bacterial count level in a sample of whey or whey constituents to be analyzed, said process comprising:

a) preparing the sample for bioluminescence measurement by aa) wherein the sample is whey, aa1) diluting the whey sample with a reagent solution containing ethoxylate of 4-(1,1,3,3-tetramethylbutyl)phenol;

aa2) separating the diluted whey sample by centrifugation into a liquid phase and an solid residue;

aa3) converting the solid residue into a suspension by adding a reagent solution containing a bacteriolytic reagent;

aa4) forming a reaction mixture by mixing the suspension with a reagent solution which hydrolyzes adenosine triphosphate;

aa5) allowing the reaction mixture from step aa4) to react for a time sufficient to hydrolyze ATP present therein and to inactivate excess adenosine triphosphate hydrolyzing reagent;

or ab1) introducing the whey constituent sample into an aqueous, isotonic salt solution;

ab2) filtering the solution containing the sample through a sterile filter;

ab3) transferring the filter with retained bacteria thereon into a nutrient solution suitable for culturing bacteria; incubating this solution for 1 to 9 hours at 28° C. to 38° C., and subsequently using the nutrient solution from above the filter as a reaction mixture for further measurement;

b) releasing bacterial adenosine triphosphate in the reaction mixture obtained from process steps aa1) to aa5) or ab1) to ab3) by treatment with a reagent which releases bacterial adenosine triphosphate;

c) adding to the reaction mixture a luciferin-luciferase reagent solution buffered to a pH value of from 7.0 to 7.9 in order to effect a bioluminescence reaction with released adenosine triphosphate;

d) photometrically quantitatively measuring light emitted during the bioluminescence reaction, and e) determining the bacterial count level in the sample to be analyzed by comparing the measured light quantity with a standard curve produced under the same conditions with a sample of similar origin having a known bacterial count level.

2. The process according to claim 1, wherein the sample is whey, and in step aa5) the reaction mixture from step aa4) is allowed to react for about 20 minutes in order to hydrolyze ATP present therein and to inactivate excess ATP hydrolyzing reagent.

3. The process according to claim 1, wherein the sample is a whey constituent, and the aqueous, isotonic solution in step ab1) is Ringer's solution.

4. The process according to claim 1, wherein the sample to be analyzed is a whey constituent.

5. The process according to claim 4, wherein the sample to be analyzed is lactose powder.

6. The process according to claim 4, wherein the sample to be analyzed is whey protein powder.

7. An analysis kit for determining the bacterial count level in whey in which a whey sample is diluted with a reagent solution containing ethoxylate of 4-(1,1,3,3-tetramethylbutyl)phenol, the diluted sample is separated by centrifugation into a liquid phase and a solid residue, the solid residue is converted to a suspension by introducing it into a reagent solution containing a bacteriolytic reagent, the suspension is mixed with an adenosine triphosphate hydrolyzing reagent solution to form a reaction mixture, the reaction mixture is allowed to react for a time sufficient to hydrolyze ATP present therein and to inactivate excess adenosine triphosphate hydrolyzing reagent, bacterial adenosine triphosphate in the reaction mixture is released by treatment with a reagent which releases bacterial adenosine triphosphate, a luciferin-luciferase reagent solution buffered to a pH of 7.0 to 7.9 is added to the reaction mixture in order to effect a bioluminescence reaction with released adenosine triphosphate, light emitted during the bioluminescence reaction is photometrically measured, and the bacterial count level in the whey sample to be analyzed is determined by comparison with a standard curve produced under the same conditions from a whey sample of similar origin having a known bacterial count; wherein said analysis kit comprises:

a) a reagent solution containing ethoxylate of 4-(1,1,3,3-tetramethylbutyl)phenol;

b) a bacteriolytically active reagent solution;

c) reagents for preparing an adenosine triphosphate hydrolyzing reagent solution, namely:

c1) somase in freeze-dried form;

c2) ethylenediaminetetraacetic acid disodium salt in solid form, and c3) a liquid solution of a reagent for releasing nucleotides from somatic cells;

d) a bacterial adenosine triphosphate releasing reagent solution;

e) a luciferin-luciferase reagent, and f) a buffer solution buffering at a pH of 7.0 to 7.9.

8. The analysis kit according to claim 7, wherein the reagent solution containing ethoxylate of 4-(1,1,3,3-tetramethylbutyl)phenol further comprises at least one chemical emulsifier or detergent.

9. The analysis kit according to claim 7, wherein the bacteriolytically active reagent solution comprises lysozyme and a chemical stabilizer.

10. An analysis kit according to claim 7, wherein the bacterial adenosine triphosphate hydrolyzing reagent solution comprises somase and a 2 to 7 wt-% solution of trichloroacetic acid containing 3 to 4 mg/ml disodium salt of ethylenediaminetetraacetic acid.

11. The analysis kit according to claim 7, wherein the buffer solution buffering at a pH of 7.0 to 7.9 is an aqueous solution comprising 25 mmole/liter N-2-hydroxyethylpiperazin-N'-2-ethanesulfonic acid buffer, 7.5 mmole/liter magnesium sulfate and 1 mmole/liter disodium salt of ethylenediaminetetraacetic acid.

* * * * *